Figure 1:
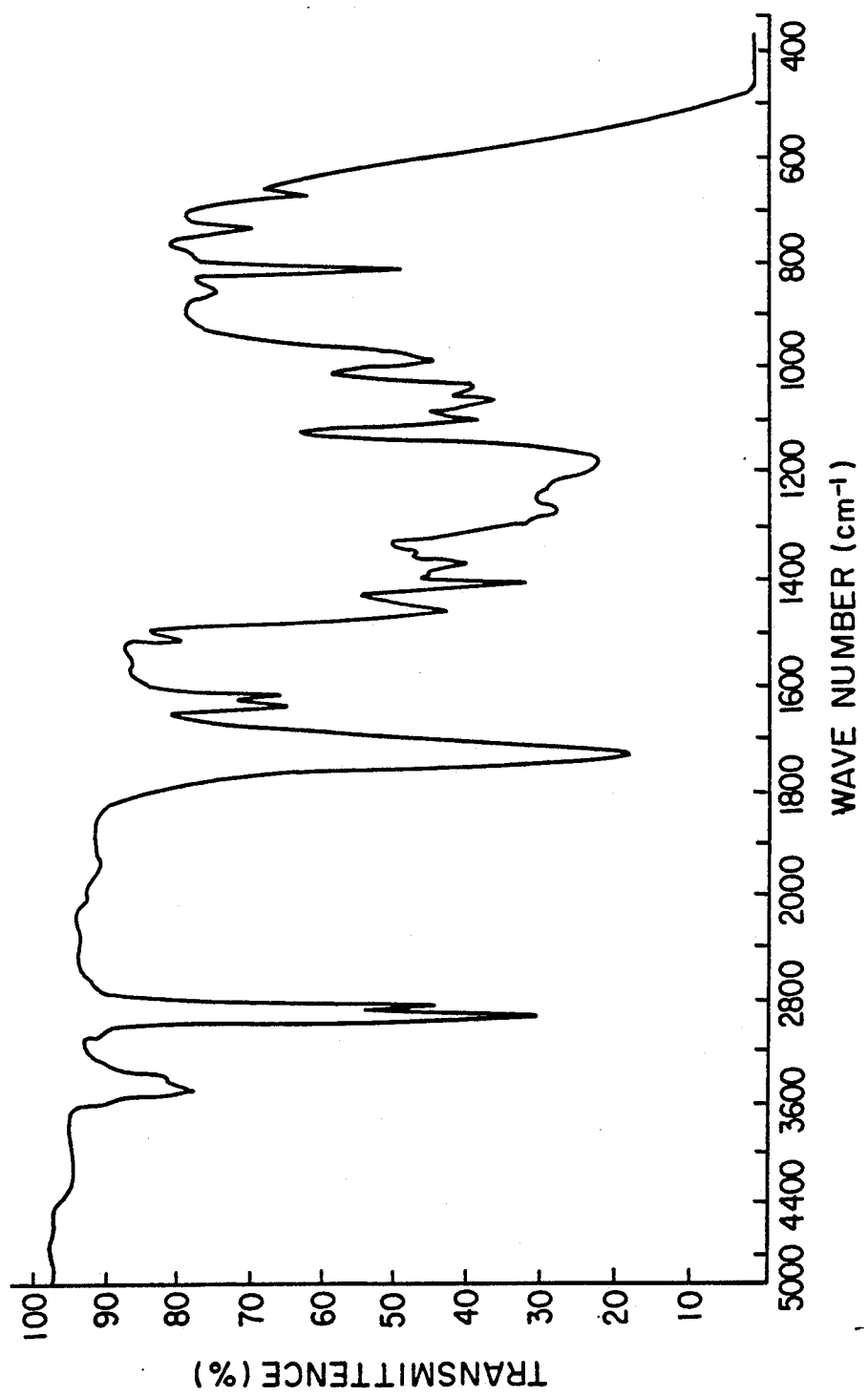

United States Patent [19]

Ohira et al.

[11] Patent Number: 5,026,807
[45] Date of Patent: Jun. 25, 1991

[54] NOVEL ESTER GROUP-CONTAINING (METH)ACRYLIC ACID ESTER, NOVEL (CO)POLYMER THEREOF, COMPOSITION COMPRISING THE (CO)POLYMER AND COMPOSITION COMPRISING THE ESTER GROUP CONTAINING (METH)ACRYLIC ACID ESTER

[75] Inventors: Yosihiro Ohira; Toshio Ohhara, both of Yokkaichi; Toshio Miyabayashi, Chiba, all of Japan

[73] Assignee: Japan Synthetic Rubber Co., Ltd., Tokyo, Japan

[21] Appl. No.: 523,180

[22] Filed: May 15, 1990

Related U.S. Application Data

[63] Continuation-in-part of Ser. No. 429,544, Oct. 31, 1989, abandoned.

[30] Foreign Application Priority Data

Oct. 31, 1988 [JP] Japan ................... 63-273330

[51] Int. Cl.$^5$ ............................................. C08F 22/10
[52] U.S. Cl. ................................... 526/321; 526/320; 526/324; 526/325
[58] Field of Search ............... 526/321, 320, 324, 325

[56] References Cited

U.S. PATENT DOCUMENTS 2,499,393  3/1950  Kenyon et al. ................ 526/321
2,559,635  7/1951  Kenyon et al. ................ 526/321

FOREIGN PATENT DOCUMENTS 0086401  8/1983  European Pat. Off. .
3513356  10/1986  Fed. Rep. of Germany .
44-20626  9/1969  Japan ........................ 526/321
47-11490  4/1972  Japan ........................ 526/321
61-53242  3/1986  Japan .
61-134350  6/1986  Japan ........................ 560/183
63-161005  7/1988  Japan ........................ 526/321

OTHER PUBLICATIONS

Journal of the Society of Rubber Industry, Japan, 53 (6) pp. 367–378 (1980).
Japanese Patent Application Kokai No. 52-98048 with its English Abstract.

Primary Examiner—Joseph L. Schofer
Assistant Examiner—N. Sarofim
Attorney, Agent, or Firm—Oblon, Spivak, McClelland, Maier & Neustadt

[57] ABSTRACT

A novel ester group-containing (meth)acrylic acid ester represented by the general formula (I):

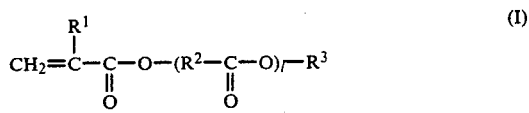

wherein $R^1$ is a hydrogen atom or a methyl group, $R^2$ is a $C_{3-20}$alkylene group, $R^3$ is a $C_{1-20}$hydrocarbon group or its derivative, and $l$ is an integer of 1–20, and a (co)polymer composed of said ester group-containing (meth)acrylic acid ester and other monomer(s) copolymerizable therewith. This (co)polymer gives a crosslinked product superior in heat resistance, low-temperature resistance and oil resistance.

10 Claims, 5 Drawing Sheets

NOVEL ESTER GROUP-CONTAINING (METH)ACRYLIC ACID ESTER, NOVEL (CO)POLYMER THEREOF, COMPOSITION COMPRISING THE (CO)POLYMER AND COMPOSITION COMPRISING THE ESTER GROUP CONTAINING (METH)ACRYLIC ACID ESTER

This application is a continuation of application Ser. No. 07/429,544, filed on Oct. 31, 1989, now abandoned.

This invention relates to a novel ester group-containing (meth)acrylic acid ester, a novel (co)polymer thereof, a composition comprising the (co)polymer and a composition comprising the ester group-containing (meth)acrylic acid ester, both the (co)polymer and the compositions being superior in heat resistance, low-temperature resistance and oil resistance and suitable for use as an industrial material.

Known rubbers which have heretofore been mainly used as industrial materials in automobile parts are natural rubber, styrene-butadiene copolymer rubber (SBR), polybutadiene rubber (BR), polyisoprene rubber (IR), butyl rubber (IIR), acrylonitrile-butadiene copolymer rubber (NBR), chloroprene rubber (CR), ethylene-propylene-diene terpolymer rubber (EPDM), acrylic rubber (ACM) and the like.

In recent years, however, these rubbers as industrial materials have been required to have higher performances which cannot be satisfied by the heat resistance, low-temperature resistance and oil resistance possessed by said conventional rubbers.

In order to improve the physical properties of the above rubbers, the polymer composition and the types and amounts of compounding agents have been mainly changed. These changes, however, have been unable to improve all of the heat resistance, low-temperature resistance and oil resistance.

For example, in the case of acrylonitrile-butadiene copolymer rubber, the oil resistance and heat resistance can be improved by increasing the acrylonitrile content, but the increase invites reduced low-temperature resistance. Hence, as a means for improving the heat resistance and oil resistance of acrylonitrile-butadiene copolymer rubber, it has been attempted to incorporate an unsaturated carboxylic acid ester into the rubber. By this method, however, the heat resistance is improved, but the low-temperature resistance and oil resistance are deteriorated.

In the case of acrylic rubber, it is known to incorporate 2-methoxyethyl acrylate as a main component monomer to improve the low-temperature resistance [Journal of the Society of Rubber Industry, Japan, 53 (6) p. 367 (1980)]. By this method, however, the oil resistance is improved but the heat resistance is deteriorated.

Under such circumstances, the present inventors have made extensive research in order to develop a rubber composition which can satisfy all of the requirements for heat resistance, low-temperature resistance and oil resistance. As a result, it has been found that a (co)polymer satisfying these requirements can be obtained by polymerizing or copolymerizing a novel ester group-containing (meth)acrylic acid ester.

An object of this invention is to provide a novel ester group-containing (meth)acrylic acid ester.

Another object of this invention is to provide a novel (co)polymer of said ester.

Still another object of this invention is to provide a composition comprising said (co)polymer.

A still further object of this invention is to provide a composition comprising the ester group-containing acrylic acid ester.

Figure 2:
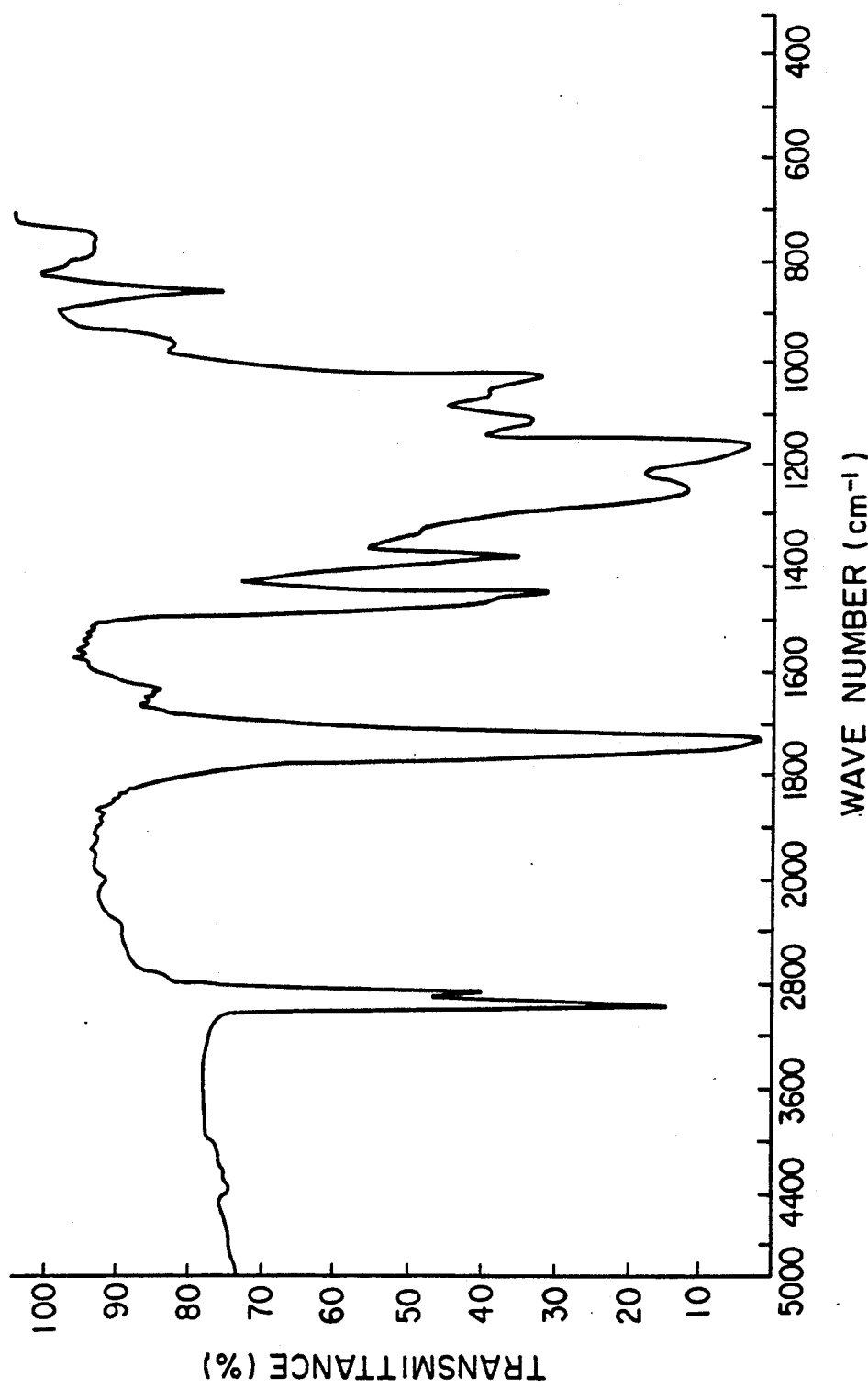
Figure 3:
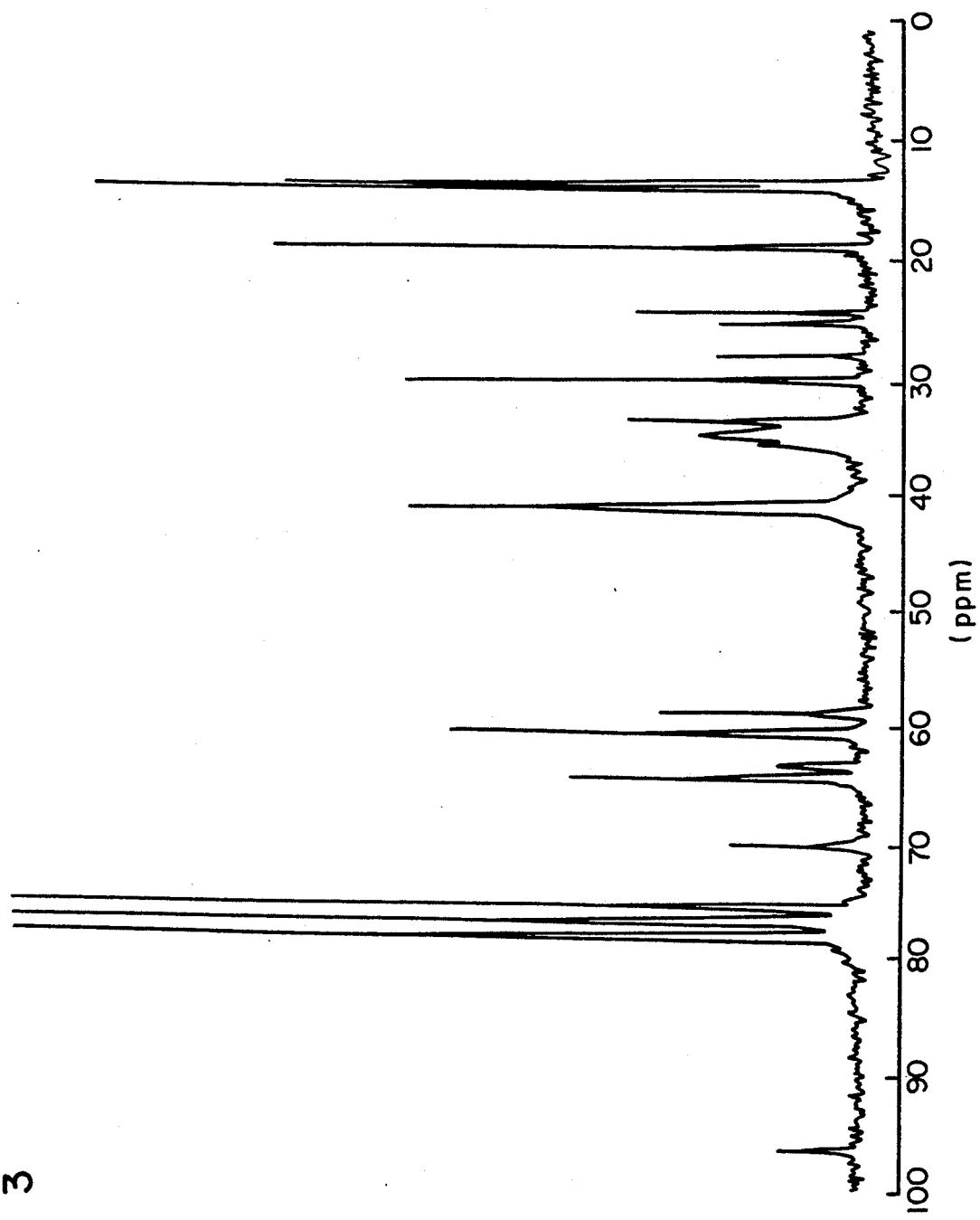
Figure 4A:
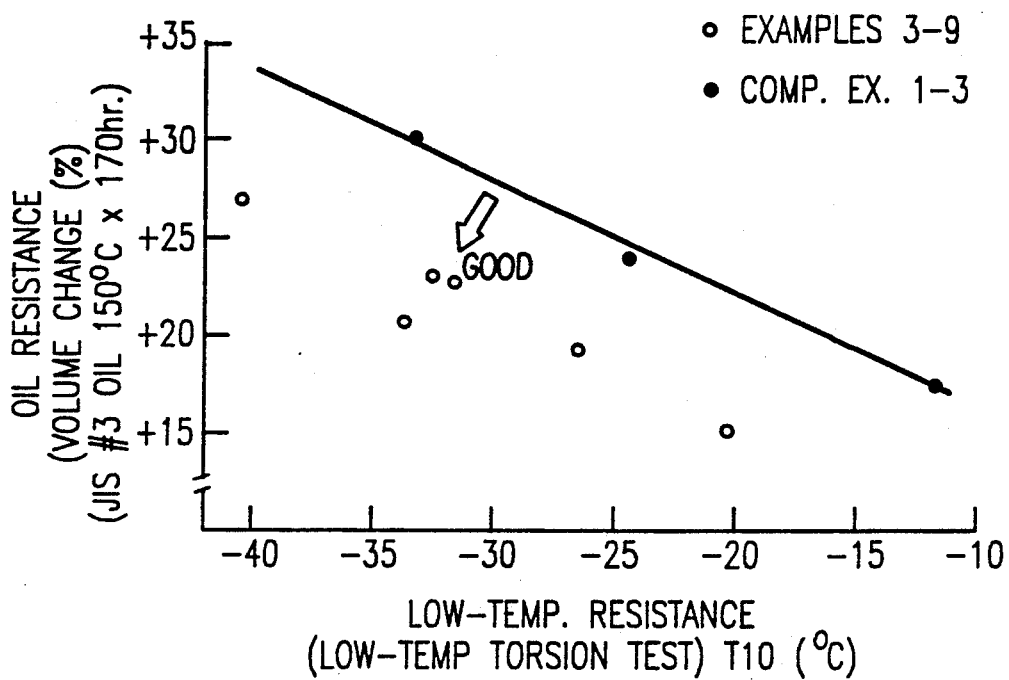
Figure 4B:
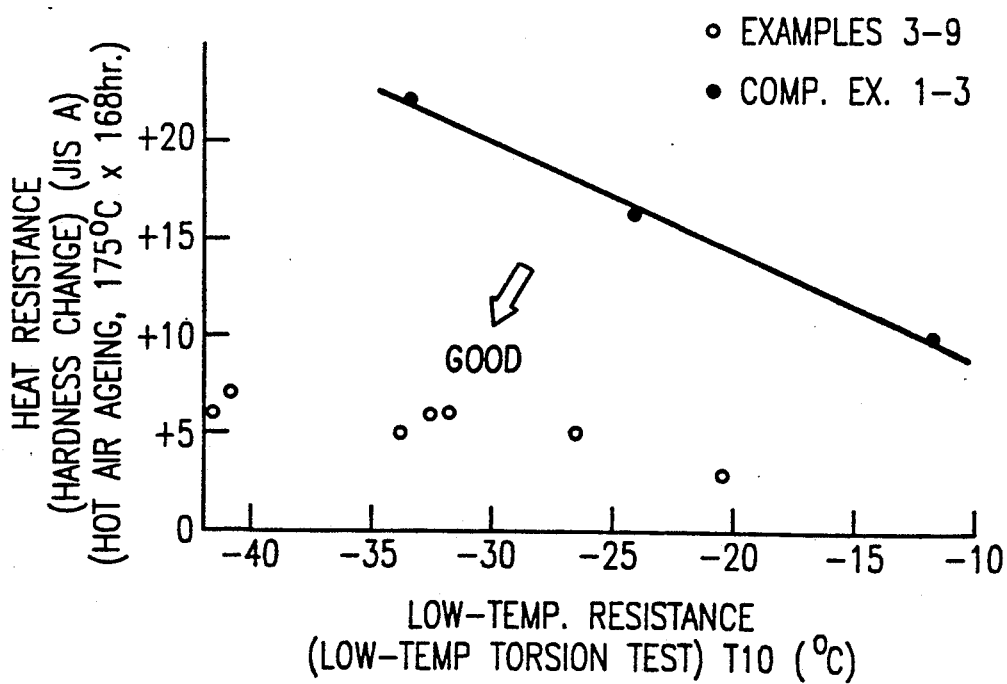
Figure 5A:
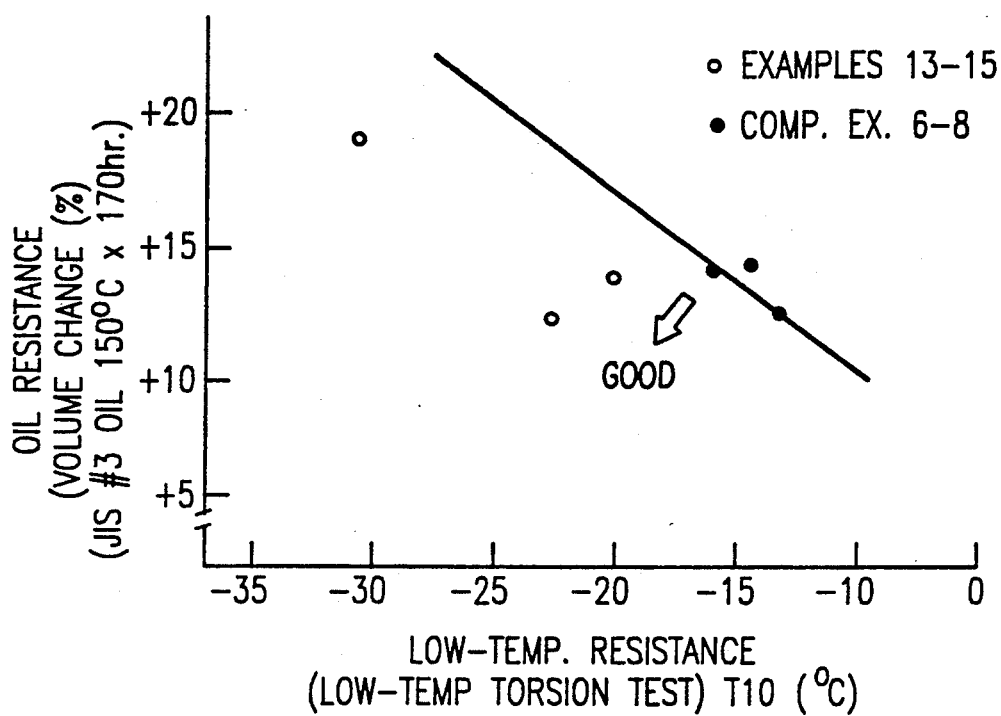
Figure 5B:
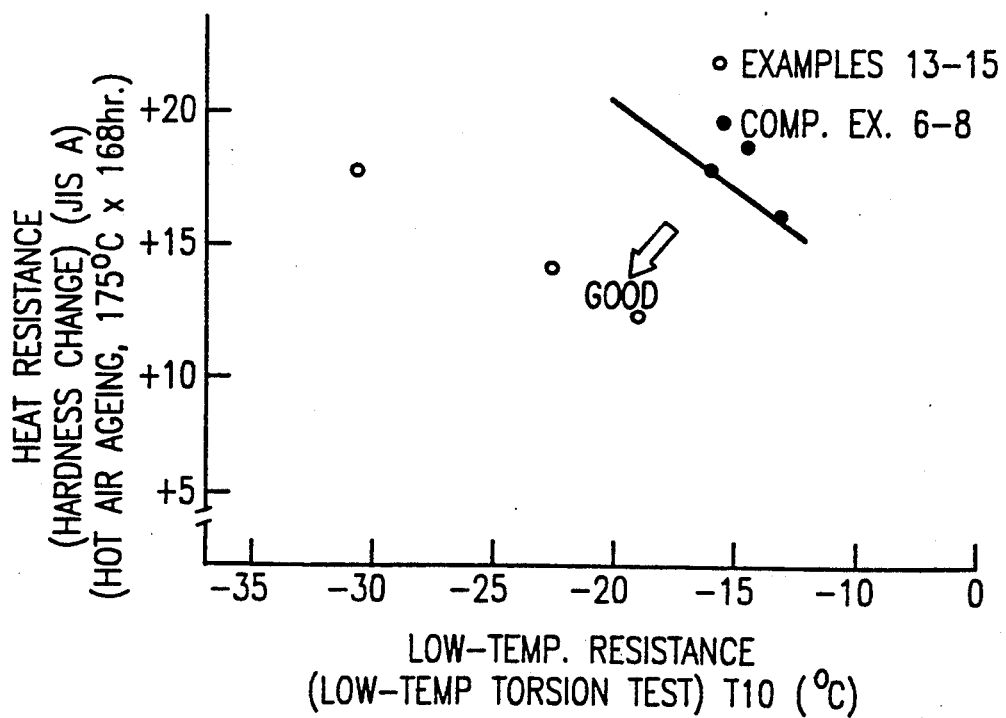

Other objects and advantages of this invention will become apparent from the following description and the accompanying drawings. In the drawings, FIG. 1 is an infrared absorption spectrum of the novel acrylic acid ester (1) obtained in Example 1; FIG. 2 is an infrared absorption spectrum of the novel acrylic acid ester copolymer obtained in Example 3; FIG. 3 is a $^{13}$C-NMR spectrum of the copolymer obtained in Example 3; FIG. 4 shows the balance of low-temperature resistance and heat resistance and the balance of low-temperature resistance and oil resistance of a composition comprising the novel acrylic acid ester copolymer; and FIG. 5 shows the balance of low-temperature resistance and heat resistance and the balance of low-temperature resistance and oil resistance of a rubber composition comprising the novel acrylic acid ester copolymer.

According to this invention, there is provided an ester group-containing (meth)acrylic acid ester [hereinafter referred to as "(meth)acrylic acid ester (I)" in some cases] represented by the general formula (I):

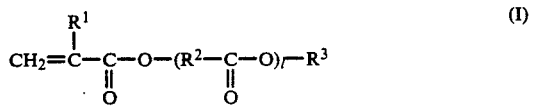

wherein
$R^1$ is a hydrogen atom or a methyl group,
$R^2$ is a $C_{3-20}$alkylene group,
$R^3$ is a $C_{1-20}$hydrocarbon group or its derivative, and l is an integer of 1-20.

According to this invention, there is further provided an ester group-containing (meth)acrylic acid ester (co)polymer (hereinafter referred to as Polymer I) composed of (A) 5-100% by weight of an ester group-containing (meth)acrylic acid ester of the general formula (I) and (B) 0-95% by weight of other monomer copolymerizable with the component (A).

According to this invention, there is still further provided an ester group-containing (meth)acrylic acid ester copolymer (hereinafter referred as Polymer II) composed of (A) 5-30% by weight of an ester group-containing (meth)acrylic acid ester of the general formula (I), (B-1) 50-90% by weight of an alkyl acrylate in which the alkyl has 3 to 20 carbon atoms [hereinafter referred to as $C_{3-20}$alkyl acrylate] and/or an alkoxy-substituted alkyl acrylate, (C) 0.1-10% by weight of a crosslinking monomer and (B-2) 0-30% by weight of other monomer copolymerizable with the components (A), (B-1) and (C).

According to this invention, there is further provided an ester group-containing (meth)acrylic acid ester copolymer (hereinafter referred to as Polymer III) composed of (A) 5-50% by weight of an ester group-containing (meth)acrylic acid ester of the general formula (I), (B-3) 10-40% by weight of butyl acrylate and/or 2-methoxyethyl acrylate, (C) 0.1-10% by weight of a crosslinking monomer and (B-4) 0-45% by weight of other monomer copolymerizable with the components (A), (B-3) and (C).

According to this invention, there is further provided an ester group-containing (meth)acrylic acid ester copolymer (hereinafter referred to as Polymer IV) composed of (A) 5-50% by weight of an ester group-containing (meth)acrylic acid ester of the general formula (I), (D) 25-60% by weight of a conjugated diene compound, (E) 20-45% by weight of an α,β-unsaturated nitrile compound and (B-5) 0-20% by weight of other monomer copolymerizable with the components (A), (D) and (E).

This invention further provides a crosslinkable (co)polymer composition comprising Polymer I, II, III or IV and a crosslinking agent.

This invention further provides a rubber composition comprising 100 parts by weight of a polymer having rubber elasticity, 5-50 parts by weight of an ester group-containing (meth)acrylic acid ester of the general formula (I) and 0.1-10 parts by weight of a crosslinking agent.

The ester group-containing (meth)acrylic acid ester of this invention is represented by the general formula (I). In the general formula (I), $R^1$ is a hydrogen atom or a methyl group, preferably a hydrogen atom.

$R^2$ is an alkylene group of 3-20 carbon atoms, preferably 3-10 carbon atoms, for example, a propylene group, a butylene group or the like.

$R^3$ is a $C_{1-20}$ hydrocarbon group or its derivative containing oxygen atom(s), nitrogen atom(s), or halogen atom(s), preferably a $C_{1-10}$ hydrocarbon group. The $C_{1-10}$ hydrocarbon group includes $C_{1-10}$ alkyl groups such as methyl, ethyl, butyl and the like; aromatic hydrocarbon groups having 6-10 carbon atoms such as phenyl, toluyl, xylyl and the like; and alicyclic hydrocarbon groups such as cyclopentyl, cyclohexyl and the like. $R^3$ is preferably a $C_{1-10}$ alkyl group, more preferably a methyl group or an ethyl group.

In the general formula (I), l is an integer of 1-20, preferably 1-10.

Specific examples of the ester group-containing (meth)acrylic acid ester represented by the general formula (I) include the following compounds:

$CH_2=CHCOO-C_3H_6COO-CH_3$,
$CH_2=CHCOO-C_4H_8COO-CH_3$,
$CH_2=CHCOO-C_5H_{10}COO-CH_3$,
$CH_2=CHCOO-C_5H_{10}COO-C_2H_5$,
$CH_2=CHCOO-C_5H_{10}COO-C_4H_9$,
$CH_2=CHCOO-C_5H_{10}COO-C_8H_{17}$,
$CH_2=CHCOO-(C_3H_6COO)_2-C_2H_5$,
$CH_2=CHCOO-(C_4H_8COO)_2-C_2H_5$,
$CH_2=CHCOO-(C_5H_{10}COO)_2-C_2H_5$,
$CH_2=CHCOO-(C_5H_{10}COO)_3-C_2H_5$,
$CH_2=CHCOO-(C_5H_{10}COO)_4-C_2H_5$,
$CH_2=CHCOO-(C_5H_{10}COO)_5-C_2H_5$,
$CH_2=CHCOO-(C_5H_{10}COO)_2-C_8H_{17}$,

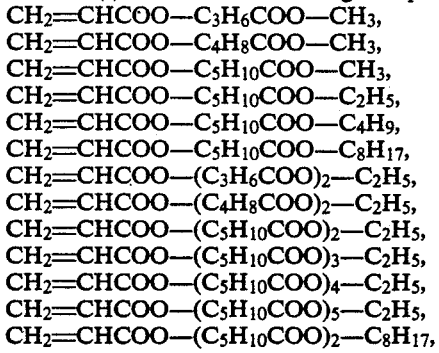

$$CH_2=\overset{CH_3}{\underset{|}{C}}-COO-(C_3H_6COO)_2-CH_3,$$

$$CH_2=\overset{CH_3}{\underset{|}{C}}-COO-(C_4H_8COO)_2-CH_3,$$

$$CH_2=\overset{CH_3}{\underset{|}{C}}-COO-(C_5H_{10}COO)_2-CH_3.$$

The (meth)acrylic acid ester (I) of this invention can be produced by, for example, an esterification reaction of an unsaturated carboxylic acid represented by the following general formula (II) [hereinafter referred to as "unsaturated carboxylic acid (II)" in some cases] and an alcohol represented by the following general formula (III) [hereinafter referred to as "alcohol (III)" in some cases]:

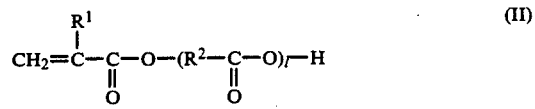

wherein $R^1$, $R^2$ and l have the same meanings as defined in the general formula (I),

wherein $R^3$ has the same meaning as defined in the general formula (I).

The alcohol (III) used in the esterification reaction includes, for example, aliphatic alcohols such as methyl alcohol, ethyl alcohol, n-propyl alcohol, n-butyl alcohol, hexyl alcohol, 2-ethylhexyl alcohol and the like; alicyclic alcohols such as cyclopentanol, cyclohexanol and the like; and aromatic alcohols such as benzyl alcohol and the like. Of these, aliphatic alcohols are preferred because the resulting (meth)acrylic acid ester (I) gives Polymer I, II, III or IV and a composition comprising said polymer, both superior in balance of oil resistance and low-temperature resistance. Methyl alcohol and ethyl alcohol are more preferable.

The above esterification reaction is effected preferably in the presence of a catalyst. The esterification catalyst includes, for example, inorganic acids such as sulfuric acid, hydrochloric acid and the like; aliphatic carboxylic acids such as formic acid, acetic acid, propionic acid and the like; aromatic sulfonic acids such as p-toluenesulfonic acid and the like; phosphorus oxychloride; polyphosphoric acid; boron trifluoride; and phosphorus pentoxide.

These catalysts can be used in an amount of ordinarily 0.01-10% by weight, preferably 0.1-5% by weight based on the total weight of the reactants [unsaturated carboxylic acid (II)+alcohol (III)].

The esterification reaction is a reversible reaction. In order to transfer the equilibrium to a product side, it is practicable, for example, to (1) use a large excess of an alcohol, (2) remove the generated water by azeotropic distillation using a solvent (benzene or toluene) and a Dean-Stark water separator, or (3) remove the generated water by refluxing a solvent using a Soxhlet's extractor containing a dessicant such as anhydrous magnesium sulfate, molecular sieve 5A or the like.

The temperature of the esterification reaction is ordinarily 0°-200° C., preferably 0°-100° C.

The esterification reaction can be effected in a solvent. As the solvent, there can be used aromatic hydrocarbons (e.g. benzene, toluene, xylene), ethers, aliphatic hydrocarbons such as n-hexane and the like, esters, etc. Of these solvents, benzene, toluene, xylene and n-hexane are preferable because they can be easily and smoothly removed out of the reaction system by azeotropic distillation with the water generated by the esterification reaction.

In order to prevent gelation due to the radical polymerization which may occur during the esterification reaction, it is preferable to add to the reaction system before the start of the reaction 50 to 1,000 ppm of a polymerization inhibitor such as hydroquinone, hydroquinone monomethyl ether, methylhydroquinone, p-benzoquinone, phenothiazine or the like.

The completion of the esterification can be confirmed by measuring the amount of the produced water removed by distillation.

The (meth)acrylic acid ester (I) can also be produced by other method, i.e. an ester exchange reaction comprising heating a (meth)acrylic acid ester represented by the following general formula (IV) with a hydroxyl group-containing ester represented by the following general formula (V) in the presence of a catalyst and distilling off the generated alcohol out of the reaction system:

wherein $R^1$ has the same meaning as defined as to the general formula (I) and $R^4$ is a $C_{1-20}$ hydrocarbon group or its derivative,

wherein $R^2$, $R^3$ and $l$ have the same meanings as defined as to the general formula (I).

The catalyst, solvent and polymerization inhibitor used in this ester exchange reaction can be the same as used in the above esterification reaction.

The (meth)acrylic acid ester (I) can be made into a homopolymer or a copolymer.

In order to obtain a copolymer, there are used two or more different (meth)acrylic acid esters (I), or a (meth)acrylic acid ester (I) and other monomer(s) copolymerizable therewith.

The content of the (meth)acrylic acid ester (I) [the component (A)] in the Polymer I is 5-100% by weight, preferably 5-50% by weight, more preferably 5-30% by weight. When the content is less than 5% by weight, the resulting polymer has no sufficient improvement in heat resistance, low-temperature resistance and oil resistance. When the content of the component (A) is too high, the resulting polymer has reduced tensile strength and is inferior in compression set at low temperatures.

Said other monomer(s) [the component (B)] copolymerizable with the (meth)acrylic acid ester (I) include, for example, unsaturated carboxylic acid esters [e.g. methyl (meth)acrylate, ethyl (meth)acrylate, propyl (meth)acrylate, n-butyl (meth)acrylate, hexyl (meth)acrylate, 2-ethylhexyl (meth)acrylate, 2-methoxyethyl (meth)acrylate, 2-ethoxyethyl (meth)acrylate, 2-butoxyethyl (meth)acrylate, cyclohexyl (meth)acrylate, benzyl (meth)acrylate, dimethyl itaconate, diethyl fumarate, di-n-butyl maleate], styrene, vinyltoluene, α-methylstyrene, vinylnaphthalene, acrylonitrile, methacrylonitrile, vinyl acetate, vinylidene chloride, vinyl chloride, isobutylene, ethylene and propylene.

The following monomers which can be used as a crosslinking site of a polymer (these monomers are hereinafter referred to as "crosslinking monomers" in some cases) are also included in the said other monomer(s) copolymerizable with the (meth)acrylic acid ester (I):

(a) diene monomers, (b) unsaturated group-containing ethylenically unsaturated carboxylic acid ester monomers, (c) epoxy group-containing ethylenically unsaturated monomers, (d) carboxyl group-containing ethylenically unsaturated monomers, (e) active, halogen-containing ethylenically unsaturated monomers, (f) hydroxyl group-containing ethylenically unsaturated monomers, and (g) amido group-containing ethylenically unsaturated monomers.

The diene monomers (a) include, for example, butadiene, ethylidenenorbornene, isoprene, piperylene, divinylbenzene, vinylcyclohexene, chloroprene, methylbutadiene, cyclopentadiene, methylpentadiene and dimethylvinylstyrylsilane. The unsaturated group-containing unsaturated carboxylic acid ester monomers (b) include, for example, ethylene glycol di(meth)acrylate, propylene glycol di(meth)acrylate, dihydrodicyclopentadienyl (meth)acrylate, dihydrodicyclopentadienyloxyethyl (meth)acrylate, vinyl (meth)acrylate and dimethylvinylmethacryloxymethylsilane. The epoxy group-containing ethylenically unsaturated monomers (c) include, for example, glycidyl (meth)acrylate and allyl glycidyl ether. The carboxyl group-containing ethylenically unsaturated monomers (d) include, for example, (meth)acrylic acid, itaconic acid, mono-n-butyl fumarate, monoethyl maleate, mono-n-butyl maleate, 2-methacryloyloxyethyl succinate, 2-methacryloyloxyethyl phthalate, 2-methacryloyloxyethyl hexahydrophthalate and 2-methacryloyloxyethyl maleate. The active, halogen-containing ethylenically unsaturated monomers (e) include, for example, 2-chloroethyl vinyl ether, vinyl chloroacetate, allyl chloroacetate and vinylbenzyl chloride. The hydroxyl group-containing ethylenically unsaturated monomers (f) include, for example, 2-hydroxyethyl acrylate, 2-hydroxypropyl methacrylate, 2-hydroxyethyl methacrylate and N-methylol (meth)acrylamide. The amido group-containing ethylenically unsaturated monomers (g) include, for example, acrylamide and methacrylamide.

The copolymerizable monomers can be used alone or in combination of two or more.

The $C_{3-20}$ alkyl acrylate and/or alkoxy-substituted alkyl acrylate [the component (B-1)] includes specifically propyl acrylate, n-butyl acrylate, hexyl acrylate, 2-ethylhexyl acrylate, 2-methoxyethyl acrylate, 2-ethoxyethyl acrylate and 2-butoxyethyl acrylate.

The component (B-2) includes the component (B) compounds other than the component (B-1) compounds.

The crosslinking monomer as the component (C) includes the crosslinking monomers included in the component (B).

The conjugated diene compound as the component (D) includes butadiene, isoprene, methylbutadiene, chloroprene, etc. included in the diene monomers of the component (B).

The α,β-unsaturated nitrile compound as the component (E) includes acrylonitrile, methacrylonitrile, etc. included in the component (B).

The component (B-4) includes the component (B) compounds other than the compounds of the components (B-1) and (C).

The component (B-5) includes the component (B) compounds other than the compounds of the components (D) and (E).

The content of the component (B-1) in Polymer II is 50-90% by weight. When the content is less than 50% by weight, the resulting polymer has reduced tensile strength or deteriorated compression set at low temperatures. When the content is more than 90% by weight, the component (A) content in the resulting polymer is small and the polymer has insufficient balance of low-temperature resistance, heat resistance and oil resistance.

The content of the component (C) in Polymers II and III is 0.1-10% by weight, preferably 0.1-5% by weight. When the content is less than 0.1% by weight, the resulting polymer has inferior tensile strength. When the content is more than 10% by weight, the polymer has reduced elongation.

The content of the component (D) in Polymer IV is 25-60% by weight. When the content is less than 25% by weight, the resulting polymer has inferior tensile strength. When the content is more than 60% by weight, the polymer has insufficient heat resistance.

The content of the component (E) in Polymer IV is 20-45% by weight. When the content is less than 20% by weight, the resulting polymer has poor oil resistance. When the content is more than 45% by weight, the polymer has insufficient low-temperature resistance.

The production of a (co)polymer of the (meth)acrylic acid ester (I) of this invention is not restricted. The (co)polymer can be easily produced according to conventional emulsion, suspension, bulk or solution polymerization preferably in the presence of a radical polymerization initiator.

When the (co)polymer is produced according to emulsion polymerization, there can be used, as the emulsifier, for example, an alkyl sulfate, an alkyl aryl sulfate and a salt of a higher fatty acid.

The (co)polymerization reaction can be effected at temperatures of $-100°$ C. to $+200°$ C., preferably 0° to 60° C.

As the radical polymerization initiator, there can be used, for example, organic peroxides such as benzoyl peroxide, cumene hydroperoxide, paramenthane hydroperoxide and the like; azo compounds such as azobisisobutyronitrile and the like; inorganic salts of persulfuric acid such as potassium persulfate, ammonium persulfate and the like; and redox type catalysts typified by a combination of an organic peroxide and iron sulfate.

The radical polymerization initiator is used ordinarily in an amount of 0.01-2% by weight based on the weight of the monomer mixture.

A molecular weight modifier (chain transfer agent) can be used if necessary. Specific examples of the modifier are t-dodecylmercaptan and dimethylxanthogen disulfide.

After the polymerization reaction has reached a desired conversion, a terminator such as N,N-diethylhydroxylamine or the like is added to the polymerization system to terminate the polymerization reaction; then, the unreacted monomers in the resulting latex are removed by steam distillation or the like; an anti-oxidant such as a phenol, an amine or the like is added to the latex; the latex is mixed with an aqueous solution of a metal salt such as aluminum sulfate, calcium chloride or the like to coagulate the latex; the coagulation product is dried to obtain a (co)polymer.

When the (co)polymer is produced according to suspension polymerization, the polymerization is effected using an oil-soluble radical initiator such as benzoyl peroxide or the like in the presence of a dispersing agent such as a saponification product of a polyvinyl alcohol; after the completion of the polymerization, water is removed to obtain a (co)polymer.

When the (co)polymer is produced according to solution polymerization, there can be employed a conventionally known method as well.

The polymerization for producing the (co)polymer can be conducted continuously or batckwise.

The molecular weight of the (co)polymer of this invention is controlled to 10,000-5,000,000, preferably 100,000-2,000,000 in terms of viscosity-average molecular weight by appropriately selecting the reaction conditions such as type and amount of molecular weight modifier, type and amount of radical initiator, polymerization temperature, type and amount of solvent, monomer concentration and the like. When the viscosity-average molecular weight of the (co)polymer is less than 10,000, the (co)polymer has inferior mechanical strengths. When the molecular weight is more than 5,000,000, the (co)polymer has poor processability.

The (meth)acrylic acid ester (I) can be made into a rubber composition by mixing with a polymer having rubber elasticity and a crosslinking agent.

The polymer having rubber elasticity used in the rubber composition of this invention includes natural rubber, styrene-butadiene copolymer rubber, polybutadiene rubber, polyisoprene rubber, butyl rubber, acrylonitrile-butadiene copolymer rubber, chloroprene rubber, ethylene-propylene-(diene) copolymer rubber, acrylic rubber, epichlorohydrin rubber, fluororubber, chlorinated polyethylene rubber, urethane rubber, etc. Of these, preferable are acrylic rubber and acrylonitrile-butadiene rubber, and more preferable is acrylic rubber.

The amount of the (meth)acrylic acid ester (I) of this invention mixed with the polymer having rubber elasticity is ordinarily 5-50 parts by weight, preferably 5-20 parts by weight, per 100 parts by weight of the polymer. When the amount is less than 5 parts by weight, the resulting rubber composition has insufficient low-temperature resistance. When the amount is more than 50 parts by weight, the rubber composition has poor mechanical strengths.

The crosslinking agent used in the rubber composition may be varied depending upon the type of the polymer in the rubber composition comprising the (meth)acrylic acid ester (I) of this invention and the type of the crosslinking monomer in the (co)polymer used in the (co)polymer composition to be described later.

For example, when the polymer having rubber elasticity used in the rubber composition of this invention is natural rubber, isoprene rubber, styrene-butadiene copolymer rubber, butadiene rubber or acrylonitrile-butadiene copolymer rubber, the crosslinking agent used in the composition is mainly sulfur, an organic sulfur-containing compound, an organic peroxide, etc. When the polymer is chloroprene rubber or chlorosulfonated polyethylene, the crosslinking agent is a metal oxide, etc. When the polymer is butyl rubber, the crosslinking agent is sulfur, quinone dioxime, a modified alkylphenolic resin, etc. When the polymer is ethylene-propylene-(diene) copolymer rubber, the crosslinking agent is sulfur, an organic peroxide, etc. When the polymer is urethane rubber, the crosslinking agent is a polyisocyanate, a polyamine, an organic peroxide, etc. When the polymer is acrylic rubber, the crosslinking agent is a metal soap and sulfur, a polyamine, an ammonium salt of an organic carboxylic acid, sulfur, a sulfur-containing compound, an organic peroxide, etc. Thus, the crosslinking agent may be varied depending upon the type of the functional group to be crosslinked, of the polymer.

In the case of the copolymer composition (to be described later) comprising, as main components, the (co)polymer of the (meth)acrylic acid ester (I) of this invention and a crosslinking agent, when the (co)polymer contains a crosslinking monomer as a comonomer, the crosslinking agent can be selected as follows:

When the crosslinking monomer is (i) a diene type monomer and/or an unsaturated group-containing unsaturated carboxylic acid ester, the crosslinking agent is sulfur, an organic sulfur-containing compound or an organic peroxide.

When the crosslinking monomer is (ii) an epoxy group-containing ethylenically unsaturated monomer, the crosslinking agent is a polyamine, a polycarboxylic acid, an acid anhydride, a polyamide, a sulfonamide, a dimethylcarbamic acid salt, an organic carboxylic acid ammonium or the like.

When the crosslinking monomer is (iii) a carboxyl group-containing ethylenically unsaturated monomer, the crosslinking agent is a polyamine, a polyepoxide, a polyol, etc.

When the crosslinking monomer is (iv) an active halogen-containing ethylenically unsaturated monomer, the crosslinking agent is a metal soap, an ammonium salt of an organic carboxylic acid, a polyamine, a polycarbamate or the like.

When the crosslinking monomer is (v) a hydroxyl group-containing ethylenically unsaturated monomer, the crosslinking agent is a polyisocyanate, a polycarboxylic acid, an alkoxymethylmelamine or the like.

When the crosslinking monomer is (vi) an amido group-containing ethylenically unsaturated monomer, the crosslinking agent is aminoformaldehyde or the like.

Of these crosslinking agents, sulfur may be any of powdery sulfur, precipitated sulfur, colloidal sulfur, insoluble sulfur and highly dispersible sulfur.

The organic sulfur-containing compound is a compound capable of liberating active sulfur upon thermal dissociation, and includes, for example, tetramethylthiuram disulfied (which is a thiuram type crosslinking acculerator) and 4,4'-dithiomorpholine.

The organic peroxide includes 2,5-dimethyl-2,5-di(t-butylperoxy)hexyne, 2,5-dimethyl-2,5-di(t-butylperoxy)hexane, 1,3-bis(t-butylperoxy)isopropylbenzene, dicumyl peroxide, dibutyl peroxide, 1,1-di-t-butylperoxy-3,3,5-trimethylcyclohexane, t-butylcumyl peroxide, t-butylperoxyisopropyl carbonate, etc.

The metal oxide includes, for example, zinc oxide, magnesium oxide and lead oxide.

The quinone dioxime includes, for example, p-quinone dioxime and p,p'-dibenzoylquinone oxime.

The modified alkylphenolic resin includes, for example, an alkylphenol-formaldehyde resin and a brominated alkylphenol-formaldehyde resin.

The polyisocyanate includes, for example, hexamethylene diisocyanate, tolylene diisocyanate and diphenylmethane diisocyanate.

The polyamine includes, for example, triethylenetatramine, methylenedianiline and diethylenetriamine.

The metal soap includes, for example, sodium stearate and potassium stearate.

The ammonium salt of an organic carboxylic acid includes, for example, ammonium benzoate and ammonium adipate.

The polycarboxylic acid includes, for example, adipic acid and octadecyldicarboxylic acid.

The acid anhydride includes, for example, pyromellitic anhydride, maleic anhydride and dodecenylsuccinic anhydride.

The dithiocarbamic acid salt includes, for example, hexamethylenediamine carbamate and zinc dimethyldithiocarbamate.

The polyepoxide includes, for example, ethylene glycol diglycidyl ether and 1,6-hexanediol diglycidyl ether.

The polyol includes, for example, 1,4-butanediol and 1,1,1-trimethylolpropane.

These crosslinking agents can be used in combination with a crosslinking accelerator in order to achieve the shortening of crosslinking time, the lowering of crosslinking temperature and the improvement of properties of crosslinked product.

For example, when sulfur is used as a crosslinking agent, there can be effectively used, as a crosslinking accelerator, for example, a thiazole (e.g. mercaptobenzothiazole), a thiuram (e.g. tetramethylthiuram disulfide), a guanidine (e.g. diphenylguanidine) or a dithiocarbamic acid salt (e.g. zinc dimethyldithiocarbamate).

When an organic peroxide is used as a crosslinking agent, there can be effectively used, as a crosslinking accelerator, ethylene glycol dimethacrylate, 1,3-butanediol dimethacrylate, 1,4-butanediol dimethacrylate, 1,6-hexanediol dimethacrylate, polyethylene glycol dimethacrylate, 1,4-butanediol diacrylate, 1,6-hexanediol diacrylate, 2,2'-bis(4-methacryloyldiethoxyphenyl)propane, trimethylolpropane trimethacrylate, trimethylolpropane triacrylate, pentaerythritol triacrylate, divinylbenzene, N,N'-methylenebisacrylamide, p-quinone dioxime, p,p'-dibenzoylquinone dioxime, triazinedithiol, triallyl cyanurate, triallyl isocyanurate, bismaleimide, a silicone oil of a high vinyl content or the like.

When a metal oxide is used as a crosslinking agent, for example, dipentamethylenethiuram tetrasulfide can be effectively used as an optional crosslinking accelerator.

When a quinone dioxime is used as a crosslinking agent, there can be effectively used, as a crosslinking accelerator, for example, an oxidizing agent such as red lead or the like.

When a modified phenolic resin is used as a crosslinking agent, there can be effectively used, as a crosslinking accelerator, for example, a halide such as chlorinated polyethylene, tin chloride or the like.

When a metal soap is used as a crosslinking agent, for example, sulfur or dipentamethylenethiuram tetrasulfide can be effectively used as a crosslinking agent.

When an amine is used as a crosslinking agent, for example, diphenylguanidine or diorthotolylguanidine can be effectively used as a crosslinking accelerator.

The amount of the crosslinking agent in the rubber composition of this invention is ordinarily 0.1–10 parts by weight per 100 parts by weight of the polymer having rubber elasticity. When the amount is less than 0.1 part by weight, crosslinking does not take place substantially. When the amount is more than 10 parts by weight, the resulting (co)polymer composition has inferior mechanical properties.

The (co)polymer of the (meth)acrylic acid ester (I) of this invention is mixed with a crosslinking agent as mentioned above, whereby a useful (co)polymer composition can be prepared. The amount of the crosslinking agent in the (co)polymer composition is ordinarily 0.1-10 parts by weight per 100 parts by weight of the (co)polymer When the amount is less than 0.1 part by weight, crosslinking does not take place substantially. When the amount is more than 10 parts by weight, the crosslinking reaction rate is too high and the resulting (co)polymer composition has inferior properties.

The rubber composition or (co)polymer composition of this invention can be prepared by mixing the respective components mentioned above and, if necessary, various compounding agents using a conventional mixer such as twin roll, Banbury mixer or the like.

Of the compounding agents, as the filler, there can be used carbon black, a white filler (e.g. silica, calcium carbonate, talc, magnesium carbonate), etc.

Of the compounding agents, as the dispersing agent, there can be used, for example, a higher fatty acid and its metal salt or its amide; as the plasticizer, there can be used, for example, a phthalic acid derivative, an adipic acid derivative and a polyether ester; as the softening agent, there can be used, for example, a lubricating oil, a process oil and a castor oil; as the anti-oxidant, there can be used, for example, an amine [e.g. 4,4'-($\alpha,\alpha$-dimethylbenzyl)diphenylamine] and an imidazole [e.g. 2,2'-methylenebis(4-methyl-6-t-butylphenol)]. Besides, there can be used a pigment, a crosslinking accelerator, a flame retardant, a foaming agent, a scorch retarder, a tackifier, a lubricant, etc. in any desired combination.

The thus obtained rubber composition or (co)polymer composition of this invention can be subjected to molding and crosslinking under the conditions for production of conventional vulcanized rubbers, to obtain a vulcanized product. That is, the composition is subjected to molding, and the molded product is subjected to primary crosslinking ordinarily at 150°-180° C. for 10-60 minutes at 50-150 kg/cm² and, if necessary, to secondary crosslinking at 150°-180° C. for 1-20 hours, whereby a vulcanized product superior in heat resistance, low-temperature resistance and oil resistance can be obtained.

The novel (meth)acrylic acid ester (co)polymer, the composition comprising said (co)polymer and the rubber composition comprising the novel (meth)acrylic acid ester, all of this invention are superior in heat resistance, low-temperature resistance and oil resistance.

The (co)polymer, the rubber composition and the (co)polymer composition, all of this invention, having such superior properties can be used in various industrial materials, for example, belt, hose, roll, packing, rubberized cloth, rubber glove, additive for synthetic resins and adhesives.

This invention is explained more specifically below referring to Examples. However, this invention is not restricted to these Examples.

In the Examples, parts and % are by weight unless otherwise specified.

In the Examples, the properties of the (meth)acrylic acid esters (I), the (co)polymers thereof and the vulcanized products of said (co)polymers were measured according to the following test methods:

Infrared spectrophotometric analysis

Apparatus: A-III infrared spectrophotometer manufactured by Nihon Bunko K.K.

The infrared spectrophotometric analysis of a (meth)acrylic acid ester (I) was effected according to a coating method, and that of a (co)polymer thereof was effected according to a KBr tablet method.

NMR analysis

Apparatus: FX 100 $^{13}$C-NMR manufactured by NEC Corp.

A polymer was dissolved in chloroform and measured for $^{13}$C-NMR spectrum. The assignment of the peak(s) of the spectrum obtained was made based on Chemical Shift Ranges in Carbon-13 NMR Spectroscopy (Wolfgang Bremser Burghard Franke Hans Wagner).

Determination of amount of vinyl chloroacetate

This was made by determining the chlorine content of a polymer according to fluorescent X-ray analysis.

Determination of amount of allyl glycidyl ether

This was made by dissolving a polymer in chloroform and then determining its epoxy equivalent according to an acetic acid method.

Determination of amounts of vinyl acrylate and dihydrodicyclopentadienyloxyethyl acrylate This was made by dissolving a polymer in chloroform and then determining its iodine value according to iodometry.

Elementary analysis

Apparatus: CHN-CORDER-MF3 manufactured by Yanagimoto Seisakusho K.K.

A sample was burnt in air at 950° C. for 5 minutes and the composition of carbon atoms and hydrogen atoms was determined.

Intrinsic viscosity

Apparatus: Constant temperature water bath

A polymer was dissolved in chloroform and then measured for viscosity using an Ubbellohde viscometer.

Acid value

A sample was dissolved in ethyl alcohol and measured for acid value by neutralization titration.

Properties of vulcanized rubber

A rubber sheet was prepared from a rubber composition comprising the (meth)acrylic acid ester (I) or a rubber composition comprising a (co)polymer of the (meth)acrylic acid ester (I). The rubber sheet was then crosslinked by a crosslinking press for a given period of time and, if necessary, further crosslinked by a Geer oven for a given period of time.

The resulting vulcanized sheet or block was subjected to molding by Dumbbell cutter and measured for heat resistance, low-temperature resistance and oil resistance according to JIS K 6301.

EXAMPLE 1

(Preparation of novel acrylic acid ester)

In a flask provided with a stirrer and a Dean-Starke water separator were placed 300 g of an unsaturated carboxylic acid having the following structural formula (M-5300, a product of TOAGOSEI CHEMICAL INDUSTRY CO., LTD.)

$CH_2=CHCOO(C_5H_{10}COO)_nH$ (n is 1-5), 138 g of ethyl alcohol, 1 cc of concentrated sulfuric acid and 300 cc of toluene.

The resulting mixture was refluxed with heating and the water generated was separated from the water separator. Heating was continued until the generation of water was no longer seen. The reaction mixture was allowed to cool to room temperature. Then, the reaction mixture in the flask was washed with 500 cc of water, 500 cc of 1% sodium hydrogen-carbonate and 500 cc of water in this order, followed by drying with anhydrous sodium sulfate. Unreacted ethyl alcohol and toluene were removed by distillation under reduced pressure to obtain a colorless viscous, liquid product in a 80% yield. This product is named as novel acrylic acid ester (1).

The structure of this novel acrylic acid ester (1) was confirmed as follows.

The unsaturated carboxylic acid used as a material and the novel acrylic acid ester (1) were measured for acid value. As a result, the unsaturated carboxylic acid had an acid value of 190 mg KOH/g and the novel acrylic acid ester (1) had an acid value of 0.5 mg KOH/g.

Next, the infrared absorption spectrum of the novel acrylic acid ester (1) is shown in FIG. 1. The elementary analysis of the novel acrylic acid ester (1) gave a carbon content of 62.2% and a hydrogen content of 8.5%.

From the results of the acid values, the infrared absorption spectrum and the elementary analysis, the novel acrylic acid ester (1) was judged to be represented by the following formula:

$CH_2=CHCOO(C_5H_{10}COO)_n-C_2H_5$ (n=1-5)

EXAMPLE 2

(Preparation of novel acrylic acid ester)

The same procedure as in Example 1 was repeated, except that 387 g of 2-ethylhexyl alcohol was used in place of the ethyl alcohol, to obtain a colorless viscous liquid product in a 78% yield. This product was named as novel acrylic acid ester (2). The structure of this ester was confirmed in the same manner as in Example 1.

From the results of the acid values, the infrared absorption spectrum and the elementary analysis, the novel acrylic acid ester (2) was judged to be represented by the following formula:

$CH_2=CHCOO(C_5H_{10}COO)_n-C_8H_{17}$ (n=1-5)

EXAMPLE 3

(Preparation of novel acrylic acid ester copolymer and composition comprising said copolymer)

Into an autoclave purged with nitrogen were charged 100 parts of a monomer mixture, 4 parts of sodium laurylsulfate, 0.25 part of p-menthane hydroperoxide, 0.01 part of ferrous sulfate, 0.025 part of sodium ethylenediaminetetraacetate and 0.04 part of sodium formaldehyde sulfoxylate. The resulting mixture was subjected to reaction at 30° C. until the conversion of the monomers reached 90%. Then, 0.5 part of N,N-diethylhydroxylamine was added to terminate the reaction.

The reaction mixture was taken out, and steam was blown thereinto to remove the unreacted monomers. The resulting rubber latex was added to a 0.25% aqueous calcium chloride solution for coagulation. The coagulation product was washed with water thoroughly and dried at about 90° C. for 3 hours to obtain a copolymer (hereinafter referred to as copolymer A).

The infrared absorption spectrum of the copolymer A is shown in FIG. 2. In FIG. 2, there are observed a stretching vibration of $>C=O$ (ester group) at 1,730 $cm^{-1}$ and a stretching vibration of methylene group at 2,950–2,850 $cm^{-1}$.

The $^{13}C$-NMR spectrum of the copolymer A is shown in FIG. 3.

The composition of the copolymer A was calculated from the chemical shift of the $^{13}C$-NMR spectrum. Exceptionally, the vinyl chloroacetate content was determined according to fluorescent X-ray analysis. The results are shown in Table 1.

The viscosity-average molecular weight [M] of the copolymer A was measured as follows. The result obtained is shown in Table 1.

$[\eta]=31.4\times10^{-3}[M]^{0.68}$ (ml/g)

[Polymer Handbook IV-10, 1975, J. Brandrup, E. H. Immergut, A Wiley-Interscience Publication]

The copolymer A was kneaded with the crosslinking agent and others shown in Table 2 to obtain a novel acrylic acid ester copolymer composition.

The composition was crosslinked. The properties of the vulcanized rubber were measured according to JIS K 6301. The results obtained are shown in Table 2.

EXAMPLES 4–9 AND COMPARATIVE EXAMPLES 1–3

(Preparation of novel acrylic acid ester copolymer, composition comprising said copolymer, comparative copolymer and comparative composition comprising said comparative copolymer)

A monomer mixture as shown in the polymer composition of Table 1 was subjected to reaction under the same conditions as in Example 3 using the same reactor as in Example 3 to obtain a copolymer (hereinafter referred to as copolymers B-J).

The compositions and molecular weights of the copolymers B-J were determined in the same manner as in Example 3. The amount of allyl glycidyl ether was determined by determining the amount of the epoxy group, and the amounts of vinyl acrylate and dihydrodicylopentadienyloxyethyl acrylate were determined by iodometry.

The compositions of the copolymers B-J are shown in Table 1. The compounding recipes and vulcanized rubbers of the compositions comprising the copolymers B-J are shown in Table 2. The properties of the crosslinked products of said compositions are shown in Table 2 and FIG. 4.

As is clear from these results, the novel acrylic acid ester copolymer compositions of this invention are superior to conventional copolymer compositions in heat resistance, low-temperature resistance and oil resistance.

EXAMPLES 10–12 AND COMPARATIVE EXAMPLES 4–5

(Preparation of novel acrylic acid ester copolymer, composition comprising said copolymer, comparative copolymer and comparative composition comprising said comparative copolymer)

In the same manner as in Example 3, a monomer mixture as shown in the polymer composition of Table 3 was subjected to reaction until a conversion of 80% was reached, to obtain a copolymer (hereinafter referred to as copolymers K-O).

The compositions of the copolymers K-O were determined from the $^{13}$C-NMR spectra in the same manner as in Example 3. The results obtained are shown in Table 3.

The viscosity-average molecular weights [M] of the copolymers K-O were measured as follows, to obtain the results shown in Table 3:

$[\eta] = 54 \times 10^{-3}[M]^{0.68}$ (ml/g)

[Polymer Handbook IV-10, 1975, J. Brandrup, E. H. Immergut, A Wiley-Interscience Publication]

To 100 parts of each of the copolymers K-O were added 5 parts of zinc oxide, 1 part of stearic acid, 60 parts of SRF carbon black, 5 parts of dioctyl phthalate, 0.5 part of sulfur, 1.5 parts of tetramethylenethiuram disulfide and 2.0 parts of N-cyclohexyl-2-benzothiazyl-sulfenamide. They were mixed by a roll. The mixture was crosslinked by a press at 160° C. for 20 minutes to prepare a crosslinked sheet. The properties of the crosslinked product were measured in the same manner as in Example 3. The results are shown in Table 3.

As is clear from Table 3, the novel acrylic acid ester copolymer compositions of this invention are superior to conventional acrylic acid ester copolymer compositions in balance of heat resistance, low-temperature resistance and oil resistance.

EXAMPLES 13–15 AND COMPARATIVE EXAMPLES 6–8

(Preparation of rubber composition comprising novel acrylic acid ester copolymer and comparative rubber composition)

The copolymer H or I shown in Table 1 and various compounding agents shown in Table 4 were kneaded by a roll to obtain a rubber composition. From this rubber composition was prepared a crosslinked sheet. The crosslinked sheet properties were measured in the same manner as in Example 3. The results obtained are shown in Table 4 and FIG. 5. As is clear from Table 4, the rubber compositions comprising the novel acrylic acid ester of this invention as an essential component are superior to conventional rubber compositions in balance of heat resistance, low-temperature resistance and oil resistance.

EXAMPLES 16–17 AND COMPARATIVE EXAMPLES 9–10

(Preparation of rubber composition comprising novel acrylic acid ester and comparative rubber composition)

Using an NBR (as a copolymer) and various compounding agents as shown in Table 5 and employing the same procedure as in Example 13, rubber compositions were prepared. The compositions were crosslinked and the crosslinked products were measured for properties. The results are shown in Table 5.

As is clear from Table 5, the rubber compositions comprising the novel acrylic acid ester of this invention as an essential component are superior to conventional rubber compositions in balance of heat resistance, low-temperature resistance and oil resistance.

TABLE 1

| Name of Copolymer | A | B | C | D | E | F | G | H | I | J |
|---|---|---|---|---|---|---|---|---|---|---|
| Polymer composition (%) | | | | | | | | | | |
| Ethyl acrylate | 38 | 53 | 38 | 36.5 | 36.5 | 35 | 77 | 98 | 30 | — |
| n-Butyl acrylate | 20 | 23 | 10 | 28 | 28 | 28 | — | — | 43 | 48 |
| 2-Methoxyethyl acrylate | 15 | 12 | — | 10 | 10 | 10 | — | — | 25 | 50 |
| Vinyl chloroacetate | 2 | 2 | 2 | — | — | 2 | — | 2 | 2 | 2 |
| Vinyl acrylate | — | — | — | — | 0.2 | — | — | — | — | — |
| Allyl glycidyl ether | — | — | — | 0.5 | — | — | — | — | — | — |
| Dihydrodicyclopenta-dienyloxyethyl acrylate | — | — | — | — | — | — | 3 | — | — | — |
| Novel acrylic acid ester (1) | 25 | 10 | 50 | 25 | 25 | — | 20 | — | — | — |
| Novel acrylic acid ester (2) | — | — | — | — | — | 25 | — | — | — | — |
| Total | 100 | 100 | 100 | 100 | 100 | 100 | 100 | 100 | 100 | 100 |
| Intrinsic viscosity [η] (dl/g) | 2.8 | 4.1 | 1.8 | 2.9 | 1.6 | 1.9 | 3.0 | 4.0 | 2.1 | 4.4 |
| Viscosity-average molecular weight (× 10$^4$) | 64 | 113 | 34 | 68 | 16 | 36 | 71 | 109 | 42 | 125 |

TABLE 2

| | Example 3 | Example 4 | Example 5 | Example 6 | Example 7 |
|---|---|---|---|---|---|
| Compounding recipe (parts) | | | | | |
| Copolymer name | A | B | C | D | E |
| Copolymer amount | 100 | 100 | 100 | 100 | 100 |
| Carbon Black (HAF) | 50 | 50 | 50 | 50 | 50 |
| Stearic acid | 1 | 1 | 1 | 1 | 1 |
| Sodium stearate | 2.5 | 2.5 | 2.5 | — | — |
| Potassium stearate | 0.5 | 0.5 | 0.5 | — | — |
| Sulfur | 0.3 | 0.3 | 0.3 | — | — |
| PERKADOX 14/40*[1] | — | — | — | — | 1.5 |
| VULNOC PM*[2] | — | — | — | — | 1.5 |
| VULNOC AB*[3] | — | — | — | 1.5 | — |
| Vulcanization accelerator*[4] | — | — | — | — | — |

TABLE 2-continued

| Crosslinking conditions | | | | | |
|---|---|---|---|---|---|
| Primary crosslinking (press) | 170° C. × 20 minutes | | | | |
| Secondary crosslinking (oven) | 175° C. × 4 hours | | | | |
| Properties of vulcanized rubber | | | | | |
| Heat resistance (175° C. × 168 hours, hot air aging) Hardness change (JIS A) | +5 | +5 | +6 | +6 | +6 |
| Low-temperature resistance (low-temperature torsion test) $T_{10}$ (°C.) | −33.8 | −26.5 | −41.5 | −32.5 | −31.9 |
| Oil resistance (JIS #3 oil, 150° C. × 70 hours) Volume change (%) | +24.0 | +22.6 | +18.0 | +26.0 | +25.8 |

| | Example 8 | Example 9 | Comparative Example 1 | Comparative Example 2 | Comparative Example 3 |
|---|---|---|---|---|---|
| Compounding recipe (parts) | | | | | |
| Copolymer name | F | G | H | I | J |
| Copolymer amount | 100 | 100 | 100 | 100 | 100 |
| Carbon Black (HAF) | 50 | 50 | 50 | 50 | 50 |
| Stearic acid | 1 | 1 | 1 | 1 | 1 |
| Sodium stearate | 2.5 | — | 2.5 | 2.5 | 2.5 |
| Potassium stearate | 0.5 | — | 0.5 | 0.5 | 0.5 |
| Sulfur | 0.3 | 0.4 | 0.3 | 0.3 | 0.3 |
| PERKADOX 14/40*[1] | — | — | — | — | — |
| VULNOC PM*[2] | — | — | — | — | — |
| VULNOC AB*[3] | — | — | — | — | — |
| Vulcanization accelerator*[4] | — | 0.75 | — | — | — |
| Crosslinking conditions | | | | | |
| Primary crosslinking (press) | | | | | |
| Secondary crosslinking (oven) | | | | | |
| Properties of vulcanized rubber | | | | | |
| Heat resistance (175° C. × 168 hours, hot air aging) Hardness change (JIS A) | +7 | +3 | +10 | +16 | +22 |
| Low-temperature resistance (low-temperature torsion test) $T_{10}$ (°C.) | −40.5 | −20.4 | −12.0 | −24.2 | −33.4 |
| Oil resistance (JIS #3 oil, 150° C. × 70 hours) Volume change (%) | +30.2 | +18.1 | +17.5 | +24.1 | +30.0 |

Note:
*[1]: 1,3-Bis(t-butylperoxyisopropyl)benzene (a product of Kayaku Noury Co., Ltd.)
*[2]: N,N'-m-phenylenedimaleimide (a product of Ohuchi Shinko Chemical Industrial Co., Ltd.)
*[3]: Ammonium benzoate (a product of Ohuchi Shinko Chemical Industrial Co., Ltd.)
*[4]: Tetramethylthiuram disulfide

TABLE 3

| | Example | | | Comparative Example | |
|---|---|---|---|---|---|
| | 10 | 11 | 12 | 4 | 5 |
| Name of copolymer | K | L | M | N | O |
| Polymer composition (%) | | | | | |
| Butadiene | 60 | 25 | 60 | 60 | 25 |
| Acrylonitrile | 30 | 25 | 30 | 30 | 25 |
| Butyl acrylonitrile | — | — | — | 10 | 50 |
| Novel acrylic acid ester (1) | 10 | 50 | — | — | — |
| Novel acrylic acid ester (2) | — | — | 10 | — | — |
| Total | 100 | 100 | 100 | 100 | 100 |
| Intrinsic viscosity [η] (dl/g) | 5.6 | 3.8 | 4.9 | 6.3 | 4.6 |
| Viscosity-average molecular weight (× 10⁴) | 80 | 45 | 66 | 96 | 60 |
| Properties of vulcanized rubber | | | | | |
| Heat resistance (130° C. × 70 hours, hot air aging) Elongation change (%) | −27 | −12 | −28 | −36 | −22 |
| Low-temperature resist- | −28.5 | −35.4 | −30.2 | −25.0 | −19.5 |

TABLE 3-continued

| | Example | | | Comparative Example | |
|---|---|---|---|---|---|
| | 10 | 11 | 12 | 4 | 5 |
| ance (low-temperature torsion test) $T_{10}$ (°C.) | | | | | |
| Oil resistance (JIS #3 oil, 120° C. × 70 hours) Volume change (%) | +18.5 | +12.4 | +19.6 | +22.5 | +17.0 |

TABLE 4

| | Example 13 | Example 14 | Example 15 | Comparative Example 6 | Comparative Example 7 | Comparative Example 8 |
|---|---|---|---|---|---|---|
| Compounding recipe (parts) | | | | | | |
| Copolymer name | H | H | I | H | H | H |
| Copolymer amount | 100 | 100 | 100 | 100 | 100 | 100 |
| HAF carbon black | 50 | 50 | 50 | 50 | 50 | 50 |
| Novel acrylic acid ester (1) | 10 | 20 | 10 | — | — | — |
| RS-700[*1] | — | — | — | 10 | — | — |
| RS-107[*2] | — | — | — | — | 10 | — |
| C-8[*3] | — | — | — | — | — | 10 |
| Stearic acid | 1.0 | 1.0 | 1.0 | 1.0 | 1.0 | 1.0 |
| Sodium stearate | 2.5 | 2.5 | 2.5 | 2.5 | 2.5 | 2.5 |
| Potassium stearate | 0.5 | 0.5 | 0.5 | 0.5 | 0.5 | 0.5 |
| Sulfur | 0.3 | 0.3 | 0.3 | 0.3 | 0.3 | 0.3 |
| Crosslinking conditions | | | | | | |
| Primary crosslinking (press) | 170° C. × 20 minutes | | | | | |
| Secondary crosslinking (oven) | 175° C. × 4 hours | | | | | |
| Properties of vulcanized rubber | | | | | | |
| Heat resistance (175° C. × 168 hours, hot air aging) Hardness change (JIS A) | +12 | +14 | +18 | +18 | +19 | +16 |
| Low-temperature resistance (low-temperature torsion test) $T_{10}$ (°C.) | −19.2 | −23.8 | −30.8 | −16.2 | −14.8 | −13.5 |
| Oil resistance (JIS #3 oil, 150° C. × 70 hours) Volume change (%) | +13.3 | +11.8 | +19.1 | +13.8 | +14.0 | +12.0 |

Note:
[*1]: Polyether ester (a product of Adeka Argus Chemical Co., Ltd.)
[*2]: Dibutylcarbitol adipate (a product of Adeka Argus Chemical Co., Ltd.)
[*3]: Trioctyl trimellitate (a product of Adeka Argus Chemical Co., Ltd.)

TABLE 5

| | Example 16 | Example 17 | Comparative Example 9 | Comparative Example 10 |
|---|---|---|---|---|
| Compounding recipe (parts) | | | | |
| Copolymer name | N230S[*1] | N220S[*2] | N230S | N220S |
| Copolymer amount | 100 | 100 | 100 | 100 |
| SRF carbon black | 60 | 60 | 60 | 60 |
| Novel acrylic acid ester (1) | 10 | 10 | — | — |
| Dioctyl phthalate | — | — | 10 | 10 |
| Stearic acid | 1.0 | 1.0 | 1.0 | 1.0 |
| Zinc oxide | 5.0 | 5.0 | 5.0 | 5.0 |
| Sulfur | 0.5 | 0.5 | 0.5 | 0.5 |
| TT | 1.5 | 1.5 | 1.5 | 1.5 |
| CZ | 2.0 | 2.0 | 2.0 | 2.0 |
| Crosslinking conditions | 160° C. × 20 minutes, crosslinking by press | | | |
| Properties of vulcanized rubber | | | | |
| Heat resistance (130° C. × 170 hours, hot air aging) Hardness change (JIS A) | −34 | −29 | −54 | −46 |
| Low-temperature resistance (low-temperature torsion test) $T_{10}$ (°C.) | −29.8 | −24.2 | −26.4 | −20.5 |
| Oil resistance (JIS #3 oil, 120° C. × 70 hours) Volume change (%) | +12.6 | +7.0 | +15.0 | +8.0 |

Note:
[*1]: Acrylonitrile-butadiene copolymer rubber (a product of Japan Synthetic Rubber Co., Ltd.)
[*2]: Acrylonitrile-butadiene copolymer rubber (a product of Japan Synthetic Rubber Co., Ltd.)

EXAMPLES 18–25

(Preparation of novel acrylic acid ester copolymer, composition comprising said copolymer)

A monomer mixture as shown in the polymer composition of Table 6 was subjected to reaction under the same conditions as in Example 3 using the same reactor as in Example 3 to obtain a copolymer (hereinafter referred to as copolymers P-W).

The compositions and molecular weights of the copolymers P-W were determined in the same manner as in Example 3. The amount of allyl glycidyl ether was determined by determining the amount of the epoxy group, and the amounts of vinyl acrylate were determined by iodometry.

The compositions of the copolymers P-W are shown in Table 6. The compounding recipes and vulcanized rubbers of the compositions comprising the copolymers P-W are shown in Table 7. The properties of the crosslinked products of said compositions are shown in Table 7.

As is clear from these results, the novel acrylic acid ester copolymer compositions of this invention are superior in heat resistance, low-temperature resistance, oil resistance and compression set.

ester group-containing (meth)acrylic acid ester of the general formula (I)

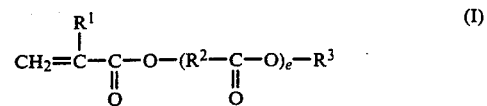

wherein $R^1$ is a hydrogen atom or a methyl group, $R^2$ is a $C_{3-20}$ alkylene group, $R^3$ is a $C_{1-20}$ hydrocarbon group or its derivative, and e is an integer of 1–20 and (B) 0–95% by weight of another monomer copolymerizable with the component (A).

2. The (co)polymer according to claim 1, wherein in the general formula (I), $R^1$ is a hydrogen atom, $R^2$ is $-C_5H_{10}-$, $R^3$ is $-C_2H_5$ or $-C_8H_{17}$, and l is 1–5.

3. An ester group-containing (meth)acrylic acid ester copolymer composed of (A) 5–30% by weight of an

TABLE 6

| Name of copolymer | P | Q | R | S | T | U | V | W |
|---|---|---|---|---|---|---|---|---|
| Polymer composition (% by wt.) | | | | | | | | |
| n-Butyl acrylate | 39 | 44 | 37 | 28 | 20 | 9 | 9 | 25 |
| 2-Ethylhexyl acrylate | — | — | — | — | 8 | — | — | — |
| 2-Methoxyethyl acrylate | 40 | 45 | 32 | 23 | 28 | — | — | 24 |
| Ethyl acrylate | — | — | 7 | 25 | 25 | 50 | 70 | — |
| Acrylic acid oligoester*[1] | 20 | 10 | 23 | 23 | 18 | 40 | 20 | 50 |
| Vinyl chloroacetate | 1.0 | 1.0 | — | 1.0 | — | 1.0 | 1.0 | 1.0 |
| Allyl glycidyl ether | — | — | — | — | 1.0 | — | — | — |
| Chloromethylstyrene | — | — | 1.0 | — | — | — | — | — |
| Total | 100 | 100 | 100 | 100 | 100 | 100 | 100 | 100 |
| Polymer Mooney viscosity $ML_{1+4}$ (100° C.) | 25.5 | 30.0 | 28.0 | 32.0 | 27.5 | 35.0 | 39.0 | 21.0 |

Note:
*[1]: $CH_2=CHCOO(C_5H_{10}COO)_n$ (n = 26 on the average)

TABLE 7

| | Example No. | | | | | | | |
|---|---|---|---|---|---|---|---|---|
| | 18 | 19 | 20 | 21 | 22 | 23 | 24 | 25 |
| Compounding recipe (parts) | | | | | | | | |
| Polymer | | | | | | | | |
| Name | P | Q | R | S | T | U | V | W |
| Amount | 100 | 100 | 100 | 100 | 100 | 100 | 100 | 100 |
| Carbon black (FEF) | 60 | 60 | 60 | 60 | 60 | 60 | 60 | 60 |
| Stearic acid | 1 | 1 | 1 | 1 | 1 | 1 | 1 | 1 |
| Sodium stearate | 2.5 | 2.5 | 2.5 | 2.5 | — | 2.5 | 2.5 | 2.5 |
| Potassium stearate | 0.5 | 0.5 | 0.5 | 0.5 | — | 0.5 | 0.5 | 0.5 |
| Sulfur | 0.3 | 0.3 | 0.3 | 0.3 | 2.0 | 0.3 | 0.3 | 0.3 |
| Crosslinking conditions | | | | | | | | |
| Primary crosslinking (press) | At 170° C. for 20 minutes | | | | | | | |
| Secondary crosslinking (oven) | At 175° C. for 4 hours | | | | | | | |
| Properties of crosslinked product | | | | | | | | |
| Low-temperature resistance | | | | | | | | |
| Impact brittleness test Tb (°C.) | −43.5 | −42.1 | −42.5 | −40.0 | −39.0 | −38.5 | −25.0 | −46.0 |
| Low temp. compression set (−30° C. × 24 hours) $C_S$ (%) | 50 | 45 | 61 | 62 | 59 | 80 | 98 | 88 |
| Heat resistance (175° C. × 16 hours, hot air aging) Hardness change (JIS A) | +6 | +7 | +6 | +0 | +7 | +8 | +8 | +9 |
| Oil resistance (JIS #3 oil, 150° C. × 70 hours) ΔV (%) | 25.0 | 24.0 | 30.0 | 23.5 | 29.5 | 31.0 | 18.5 | 38.2 |
| Physical properties in normal state | | | | | | | | |
| $T_B$ (kgf/cm²) | 120 | 135 | 135 | 105 | 131 | 95 | 145 | 80 |
| $E_B$ (%) | 215 | 210 | 200 | 180 | 250 | 170 | 240 | 180 |

What is claimed is:

1. An ester group-containing (meth)acrylic acid ester (co)polymer composed of (A) 5–100% by weight of an ester group-containing (meth)acrylic acid ester of the general formula (I) according to claim 1, (B-1) 50–90% by weight of at least one unit selected from the group consisting of an alkyl acrylate in which the alkyl has 3 to 21 carbon atoms and an alkoxy-substituted alkyl acrylate, (C) 0.1-10% by weight of a crosslinking monomer and (B-2) 0-30% by weight of other monomer copolymerizable with the components (A), (B-1) and (C).

4. An ester group-containing (meth)acrylic acid ester copolymer composed of (A) 5-50% by weight of an ester group-containing (meth)acrylic acid ester of the general formula (I) according to claim 1, (B-3) 10-40% by weight of at least one unit selected from the group consisting of butyl acrylate and 2-methoxyethyl acrylate, (C) 0.1-10% by weight of a crosslinking monomer and (B-4) 0-45% by weight of other monomer copolymerizable with the components (A), (B-3) and (C).

5. An ester group-containing (meth)acrylic acid ester copolymer composed of (A) 5-50% by weight of an ester group-containing (meth)acrylic acid ester of the general formula (I) according to claim 4, (D) 25-60% by weight of a conjugated diene compound, (E) 20-45% by weight of an α,β-ethylenically unsaturated nitrile compound and (B-5) 0-20% by weight of other monomer copolymerible with the components (A), (D) and (E).

6. A crosslinkable (co)polymer composition comprising an ester group-containing (meth)acrylic acid ester (co)polymer according to claim 1 and a crosslinking agent.

7. A crosslinkable copolymer composition comprising an ester group-containing (meth)acrylic acid ester copolymer according to claim 3 and a crosslinking agent.

8. A crosslinkable copolymer composition comprising an ester group-containing (meth)acrylic acid ester copolymer according to claim 4 and a crosslinking agent.

9. A crosslinkable copolymer composition comprising an ester group-containing (meth)acrylic acid ester copolymer according to claim 5 and a crosslinking agent.

10. A rubber composition comprising 100 parts by weight of a polymer having rubber elasticity, 5-50 parts by weight of an ester group-containing (meth)acrylic acid ester of the general formula (I) according to claim 1 and 0.1-10 parts by weight of a crosslinking agent.

* * * * *